United States Patent [19]

Juguin et al.

[11] 4,434,315

[45] Feb. 28, 1984

[54] PROCESS FOR ISOMERIZING OLEFINS

[75] Inventors: Bernard Juguin, Rueil-Malmaison; Jean Miquel, Paris, both of France

[73] Assignee: Institut Francais du Petrole, Rueil-Malmaison, France

[21] Appl. No.: 380,857

[22] Filed: May 21, 1982

[30] Foreign Application Priority Data

May 21, 1981 [FR] France ................... 81 10312

[51] Int. Cl.$^3$ ................................. C07C 5/23
[52] U.S. Cl. ................... 585/671; 208/136; 208/137; 208/138
[58] Field of Search ............ 585/671; 208/136, 137, 208/138

[56] References Cited

U.S. PATENT DOCUMENTS

| | | | |
|---|---|---|---|
| 2,281,804 | 5/1942 | Ruthruff | 585/671 |
| 3,243,472 | 3/1966 | Dinwiddie | 585/671 |
| 3,268,609 | 8/1966 | Nixen | 585/671 |
| 3,558,733 | 1/1971 | Myers | 585/671 |
| 3,558,734 | 1/1971 | Myers | 585/671 |
| 3,636,127 | 1/1972 | Ramquist et al. | 585/671 |
| 3,751,513 | 7/1973 | Tazuma | 585/671 |
| 4,038,337 | 7/1977 | Manara et al. | 585/671 |
| 4,070,306 | 1/1978 | Masologites | 585/671 |
| 4,104,321 | 8/1978 | Ward | 585/671 |

FOREIGN PATENT DOCUMENTS

| | | | |
|---|---|---|---|
| 878035 | 9/1961 | United Kingdom | 585/671 |
| 196801 | 5/1967 | U.S.S.R. | 585/671 |

Primary Examiner—Delbert E. Gantz
Assistant Examiner—Cynthia A. Prezlock
Attorney, Agent, or Firm—Millen & White

[57] ABSTRACT

Process for isomerizing linear ethylenic hydrocarbons to branched ethylenic hydrocarbons having the same number of carbon atoms in the molecule, in the presence of steam and of a catalyst containing alumina, silica and a metal or compound of a metal selected from chromium, palladium, nickel, copper and silver at critical concentrations of silica and of metal, and with a critical proportion of water with respect to the hydrocarbons.

12 Claims, No Drawings

PROCESS FOR ISOMERIZING OLEFINS

BACKGROUND OF THE INVENTION

The most economical additives used for improving the antiknock properties of motor fuels are alkyl lead derivatives, but, in view of the toxicity of lead, their use tends to decrease. Moreover, it is known that the high content of polluting products, such as residual hydrocarbons, carbon monoxide and nitrogen oxides, in the combustion gases of motor fuels, generally requires the use of catalytic mufflers, in order to lower this content of polluting products. These catalytic mufflers contain appropriate catalysts very often including among their components at least one metal from group VIII of the periodical classification of elements, said metal being, usually, platinum or another noble metal of the platinum family. Now, it is known that the lead contained in the motor fuel additives, which is conveyed by the combustion gases, quickly poisons the catalysts of the catalytic mufflers making the latter inefficient for the use to which they are destined. Metal derivatives other than lead derivatives have been tested, for example methyl-cyclopentadienyl tricarbonyl manganese (MTM), but this product has been shown to be a non-negligible polluting agent.

These various problems have led the refiners to the production of gasolines or gasoline components free of lead-containing antiknock agents (e.g., tetraethyl lead) having, nevertheless, a high octane number.

Up to now, the lead-free gasoline produced in the world has been obtained preferentially from the following techniques:
  high severity catalytic reforming of naphtha,
  alkylation with isobutane of the olefin-containing $C_3$–$C_4$ cuts from catalytic cracking, thermal cracking, coking, visbreaking and steam cracking.

Lead-free gasoline obtained by high severity catalytic reforming is not ideal as far as pollution and public health are concerned. As a matter of fact, it contains benzene whose vapor is very toxic.

On the contrary, by alkylation, there is obtained a gasoline which is satisfactory as well from an ecological point of view as from a purely technical point of view for the engine operation.

Unhappily this method is essentially limited by a lack of isobutane.

As a matter of fact, the reaction between isobutane and a $C_3$ or $C_4$-olefin is equimolecular; by calculation, it is established that theoretically 1.38 kg of isobutane is required for 1 kg of propylene or 1.035 kg of isobutane for 1 kg of butenes.

However, the olefinic cuts, produced for example by steam-cracking and catalytic cracking, suffer, as a general rule, from a heavy insufficiency of isobutane to satisfy the above-mentioned stoichiometry. For example, a typical cut issued from catalytic cracking has the following composition in percent by weight:

| | |
|---|---|
| propene | 25.00 |
| propane | 8.35 |
| isobutane | 23.35 |
| isobutene | 10.65 |
| n-1-butene | 6.65 |
| n-2-butene | 18.00 |
| n $C_4$ (n-butane) | 8.00 |

A simple calculation shows that the isobutane proportion is hardly one third of the stoichiometrical proportion of olefins.

The problem of isobutane insufficiency of $C_3$–$C_4$ cuts is well known. For example the U.S. Pat. No. 3,758,628 proposes to cope therewith by juxtaposition of a hydrocracking unit to a catalytic cracking unit. But at the present time, it is observed that the number and the capacity of the existing hydrocracking units are either stagnant or even reduced. Moreover hydrocracking is a costly operation which provides a number of products other than isobutane, which cannot always be upgraded.

It will be shown that the present process, according to the invention, provides for a beneficial use of $C_3$–$C_4$ cuts formed of the effluents of catalytic cracking or steam-cracking or coking or thermal cracking or visbreaking units.

As a matter of fact, attempts have been made these last years, to incorporate alcohols, esters, etc. in gasoline either for improving the octane number or to cope with a shortage of petroleum products, or for other purposes. Such attempts are disclosed, for example, in U.S. Pat. No. 3,726,942 and French Pat. No. 2,063,939.

Thus, methanol, which improves the octane number of gasoline, is one of the most interesting additives.

Another interesting additive is methyl-tert-butyl ether (MTBE) whose antiknock properties permit improvement of the quality of gasolines in the trade, in that its addition results in higher octane number than that obtained by use of methanol. Moreover, methyl-tert-butyl ether (MTBE) has a higher calorific value than methanol: 8,935 kcal/kg (i.e. 4.18×8,395 kJoules/kg) for MTBE as compared with 4764 kcal/kg (i.e. 4764×4.18 kJoules/kg) for methanol (as an average, the calorific value of a premium gasoline is 10,200 kcal/kg corresponding to 4.18×10,200 kJ/kg). Moreover, MTBE does not rise demixion problems in the presence of water, as it is the case for methanol. Furthermore, the solubility in water of MTBE is substantially higher than that of water in hydrocarbons and, accordingly, the addition of MTBE improves the compatibility with water of motor fuels.

MTBE has other advantages:
  its boiling point corresponds to that of the gasoline components having the lower antiknock properties;
  its vapor pressure is not a disadvantage,
  it has an excellent freezing point,
  its solubility in water is relatively low and, as it is completely miscible (with) all the hydrocarbons, it has but little liability of causing problems of phase separation in motor fuel mixtures, even in the presence of water.

Briefly stated, MTBE appears as a very interesting additive for improving the qualities of gasoline. This product is generally obtained from isobutene and methanol according to the following balanced reaction:

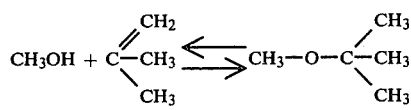

A source of isobutene is the isobutene contained in $C_3$–$C_4$ olefinic cuts issued from effluents of catalytic cracking, steam-cracking, coking, visbreaking and thermal cracking (another source of isobutene is the fraction issued from an effluent of a MTBE producing unit, this fraction being obtained after treatment of said effluent so as to remove therefrom the produced MTBE, optionally withdrawing the paraffins contained therein and optionally hydrogenating the butadiene).

However, it must be observed that a production of 100 000 T/year of MTBE from, for example, a $C_3$–$C_4$ steam-cracking cut, requires a cracking unit producing 500 000 T/year of ethylene, and that in the olefinic $C_3$–$C_4$ cuts issued from catalytic cracking the isobutene contents are still lower than those obtained from a steam-cracking effluent.

The shortage of isobutene is thus incompatible with the extent of development of the MTBE production.

A new way of producing isobutene has thus been proposed. Instead of separating the isobutene present in the above-mentioned $C_3$–$C_4$ cuts, this method modifies the composition of the $C_4$ hydrocarbons of the olefinic $C_3$–$C_4$ cuts, by isomerizing completely or almost completely the butenes contained in the $C_3$–$C_4$ cuts to isobutene.

Many processes and many catalysts have been proposed for this purposes and particularly catalysts containing aluminas, more particularly activated aluminas (e.g. eta alumina and gamma alumina), halogenated aluminas, bauxite, aluminas treated with derivative or boron or silicium or zirconium, various silicas-aluminas, more or less complex phosphates, solid phosphoric acid, etc.

The process according to the invention is an improvement of the prior art and, particularly, of that disclosed in the following patents:

U.S. Pat. No. 2,417,647 wherein the catalyst contains fluorinated alumina whose hydrofluoric acid content is from about 0.5 to 10%.

U.S. Pat. No. 2,395,274, wherein the catalyst is bauxite and the operation is conducted in the presence of steam.

U.S. Pat. No. 3,558,733 wherein the alumina-containing catalyst is reactivated with steam without any contact between steam and the olefins to be isomerized.

U.S. Pat. No. 3,558,734 wherein the halogenated catalyst contains about 5 to 100 ppm of water.

U.S. Pat. No. 2,422,884 wherein the operation is conducted in the presence of steam (molar ratio $H_2O$/HC varying from 0 to 10) with a boron-containing alumina catalyst.

The results obtained with these various processes are still insufficient.

Thus, the catalysts containing fluorinated alumina are not always, in the prior art, the best isomerization catalyst. In spite of a very good selectivity, they have the disadvantage, in view of their acidic properties, to activate not only the isomerization reaction but also undesirable polymerization and cracking secondary reactions which result in a lower selectivity and in a decrease of the catalyst life time. Such catalysts furthermore require a continuous introduction of fluorine to compensate for the losses of fluorine during the reaction and these catalysts also suffer from the corrosive action inherent to the fluorine derivatives.

The catalysts presently used suffer from drawbacks, the most important of which are a low selectivity, resulting from the occurrence of parasitic reactions such as cracking and polymerization, and a lack of stability resulting in a more or less rapid decrease of the conversion rate; in addition, these catalysts are difficult to regenerate or even not regenerable at all.

Furthermore, in order to obtain, with these catalysts, sufficient conversion rates the space velocities must be low enough, thus requiring the use of reactors of a large capacity.

SUMMARY OF THE INVENTION

The object of the invention is to avoid these disadvantages. It consists of operating with a catalyst containing alumina acidified with a critical amount of silica, and in presence of steam.

The use of water or steam, in the prior art, did not prove to result in sufficient improvements in olefins isomerization.

It has now been found that a convenient catalyst is obtained from alumina to which a critical amount of silica is added, provided that the operation is conducted in the presence of water, also in a critical amount.

Thus, the simultaneous presence (a) of an alumina and silica containing catalyst and (b) of water in the reaction medium, surprisingly inhibits secondary reactions.

There are thus obtained high conversion rates to the desired product, with an excellent conversion velocity and very good selectivities, while having the advantage of proceeding at lower temperatures than usual, i.e. under conditions at which the thermodynamic balance is more favorable.

DETAILED DISCUSSION

According to the process of the invention, it is possible to isomerize either a single $C_4$ olefinic cut issued from a cracking or from another reaction as above listed (after removal of the $C_3$ cut) or the totality of the $C_3$–$C_4$ olefinic cut, the $C_3$ hydrocarbons being unaffected by the isomerization of the $C_4$ hydrocarbons (butenes) and having no inconvenience for the isomerization process. The $C_3$–$C_4$ cut entirely subjected to the isomerization treatment may also, without disadvantage, include hydrocarbons containing 1, 2 and 5 to 20 carbons atoms per molecule.

According to the process of the invention, there can be isomerized other olefinic hydrocarbons containing 5 to 20 carbon atoms per molecule, having a straight chain structure, to convert them to olefinic hydrocarbons of branched structure, having the same number of carbon atoms per molecule as the olefin from which they are produced. Thus, it may be advantageous to convert pentenes to isopentene and hexenes to isohexene etc.

The preferred temperatures for conducting the present process are comprised between 300° C. and 550° C. and, more particularly, between 400° C. and 500° C. Of course, at temperatures higher than those indicated here, the isomerization reaction is still possible but, while it is more rapid than at moderate temperature, it is accompanied by secondary reactions which are undesirable, such as cracking, dehydrogenation, polymerization, coking etc. Moreover, it must be emphasized that the concentration of isoolefins (e.g. isobutenes) at equilibrium decreases with the temperature increase. But conversely, a too substantial decrease of the reaction temperature is also unsuitable since it results, on the one hand, in a lower reaction velocity and, on the other hand, in a speeding up of the polymerization reaction in spite of the fact that, generally, the polymerization velocity is not favored by a temperature decrease. By operating in conformity with the invention and preferably within the recommended temperature range, the isomerization reaction takes place at a sufficient velocity and isoolefin concentrations (e.g. isobutene concentration) very close to those corresponding to the thermodynamic equilibrium are quickly obtained while maintaining the velocity of undesirable reactions at very low levels. Of course, the precise selection of the adequate reaction temperature depends on the type of olefin to be isomerized as well as on the contact time and other varying factors.

Since an undesirable polymerization reaction is favored by a pressure increase, it is preferred to proceed at a sufficiently low pressure, generally between 0.05 MPa and 1 MPa and preferably between 0.08 and 0.4 MPa (1 MPa=10 kg/cm²).

Generally, the space velocity is from 0.1 to 10, expressed in volume of liquid olefinic charge per volume of catalyst and per hour and, preferably, from 0.5 to 4 volumes of olefins in the liquid state per volume of catalyst and per hour.

In conformity with the invention, there is admixed with the charge or added to the charge, through a separate line, the water amount required for maintaining the good selectivity of the catalyst. The amount of water introduced into the reactor is so selected as to produce in the reaction zone a molar ratio.

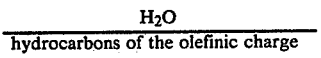

comprised between 0.1 and 10 and preferably from 0.5 to 3, more particularly from 0.8 to 2.7.

For the preparation of the catalyst, there can be used alumina of any commercial type, but preferably activated alumina, also preferably selected from the aluminas of eta or gamma type, having a low content of alkali or alkaline earth metals, for example containing less than 0.1% by weight of sodium and/or other alkali and/or alkaline earth metals.

This alumina is generally used as balls or extrudates or pellets or crushed particles, etc., of sufficient size to permit easy passage of the gaseous reactants.

The specific surface of the alumina may be advantageously from 10 to 350 m² per gram, preferably from 50 to 250 m²/g, its pore volume being, for example, from 0.4 to 0.8 cc per gram.

This alumina is activated, for example, by heating in a stream of dry air at a temperature from 350° to 550° C. for several hours.

The silica may be introduced into the alumina by any means, as a silicon derivative soluble in a convenient solvent.

For example, the alumina may be impregnated under dry conditions with an alcoholic solution of ethyl silicate, the mixture being maintained in contact for a sufficient time to achieve a good diffusion of the ethyl silicate throughout the whole pore volume of the solid.

Then, the solvent is expelled and the ethyl silicate is thereafter hydrolyzed in the presence of steam so that the formed silica becomes bound to the alumina surface. Then, the solid can, for example, be dried and thereafter roasted at a temperature comprised for example between 550° and 650° C. in the presence of air. The introduced silica amount is such that the final catalyst has a concentration of $SiO_2$ from 0.5 to 10% by weight, preferably from 1 to 6% and, more particularly from 2 to 4%.

It must nevertheless be observed that the above mentioned mode of preparation is not limitative. In fact, it is also possible to deposit silica on alumina already placed in the isomerization reaction zone.

It is thus possible, for example, to impregnate the alumina bed by introduction of an alcoholic solution containing the required amount of ethyl silicate, to expell the excess of solvent and then to proceed to the hydrolysis in the presence of steam, followed by drying in situ and calcination. The introduction of the charge follows this operation.

It is also possible to deposit the silica on alumina by passing the ethyl silicate in vapor phase through the alumina bed and to subsequently proceed to the above described operations.

Another way of operating consists of introducing the precursor, containing the silica to be deposited, in solution in the charge, etc.

In order to facilitate the regeneration of the catalyst used in the reaction, particularly by combustion of high polymerized products and even of carbon which might have been deposited on the surface of the solid during the reaction, it is convenient, in accordance with the invention, to introduce at the surface of the catalyst, an agent capable of facilitating the combustion of these organic products. As combustion activating agent, there can be used any metal or oxide or any other derivative of this metal capable of activating the oxidation reactions. By way of non limitative examples of such agents, there can be mentioned, for example, the use of at least one metal selected from the group consisting of manganese, silver, chromium, palladium, nickel, copper, the oxides of these metals etc. this list being not limitative.

Palladium is a particularly convenient agent for activating said combustion of organic products.

Thus, the addition of palladium (and the same is true with the above-mentioned other metals) results in a more facile catalyst regeneration, whereby, in particular, a temperature lower than usual can be used to start of the regeneration, the starting temperature being from 200° to 250° C. instead of 325°–375° C. When the catalyst contains palladium, the required oxygen concentration is smaller. This results in a cooler flame front than usual (this flame front, measured by thermocouple, being, without palladium, at about 400° to 450° C., which corresponds to a temperature of about 500° to 550° C. in the mass of the catalyst grain or of the catalyst ball). Thus, the addition of palladium results in a lower combustion velocity, making obvious the lower temperature increase during the regeneration. It will be observed, in addition, that a flame front of lower temperature also decreases the dangers occuring during the manipulations required by the catalyst regeneration.

The palladium may be introduced into the catalyst, for example, by impregnation with a salt of another palladium containing compound, provided that the product is soluble in water or in any other solvent. For example, palladium nitrate may be used.

The amount of metal introduced varies from about 5 ppm to about 2% by weight with respect to the catalyst. When using palladium, the introduced palladium amount is comprised between 5 and 2 000 ppm, preferably between 5 and 100 ppm. Advantageously, the palladium amount is from 10 to 30 ppm.

It must be observed that the two compounds which may be deposited on alumina, i.e. silica and an additional metal or metal compound, may optionally be introduced in a single impregnation, or in two successive impregnations with intermediary drying and roasting with the metal (e.g. palladium) is first introduced or with hydrolysis followed by a drying and roasting when silica is first deposited.

The catalyst may be used as a fixed bed, or fluid bed or moving bed.

When using a catalyst moving bed, a particular process consists of making use of several serially arranged reactors, located for example side-by-side or superposed: the charge circulates successively through each reactor by axial or radial flow. The fresh catalyst is introduced at the top of the first reactor where the fresh charge is introduced. It then flows downwardly through said reactor where from it is progressively withdrawn at the bottom and, by any convenient means (in particular, a lift in the case of side-by-side reactors), it is conveyed to the top of the next reactor wherein it also progressively flows downwardly, and so on until reaching the last reactor at the bottom of which the catalyst is also progressively withdrawn and then conveyed to the regeneration zone. At the output of the regeneration zone, the catalyst is progressively reintroduced at the top of the first reactor so as to maintain a high and substantially constant activity level at each point of the catalytic zones. The various catalyst withdrawals are effected, as above indicated, "progressively", i.e., either periodically or continuously.

The regeneration and the adjustment of tthe catalyst are effected by any known conventional means, which need not be described herein.

The catalyst used in the following examples was prepared from an alumina of the trade manufactured by Rhone-Progil and supplied as balls of 1 to 2 mm of diameter. This alumina is a cubic gamma type, its grain density is 1.23, its structural density 3.27, its total pore volume is 0.51 cc/g and its specific surface is 210 m$^2$/g.

The alkali metals content of the alumina is lower than 100 ppm and its content of alkaline-earth metals is lower than 300 ppm.

100 g of said alumina, previously roasted at 500° C., have been impregnated for 2 hours with a solution containing:

7.2 cc of pure ethyl silicate 2 cc of a palladium nitrate aqueous solution containing 0.1% of Pd and 60 cc of absolute ethyl alcohol.

The contact is maintained for 6 hours at room temperature (19° C.). Then the whole mixture is placed in an oven having a moist atmosphere (relative humidity of 90%) at 40° C. for 12 hours; the temperature is then progressively increased in 1 hour to 95° C., still under wet moist atmosphere (relative humidity of 95%) and said temperature is maintained for 12 hours. Then the whole mixture is brought to 110° C. for 12 hours under a dry atmosphere.

The dry product is then roasted at 630° C. in air.

The final catalyst has the following composition (by weight):

3% of SiO$_2$ 20 ppm of palladiumm and the balance to 100% of alumina.

EXAMPLE 1

A portion of the catalyst obtained as above is placed in a fixed bed reactor.

A C$_4$ olefinic hydrocarbon charge, whose composition is given in Table I, is passed, together with water, through said bed.

The operating conditions are as follows:

Temperature: 450° C.

Pressure: 0.1 MPa (1 kg/cm$^2$)

C$_4$ liquid charge volume per volume of catalyst and per hour: 2

Molar ratio H$_2$O/HC of the olefinic cut: 1.35

Table I also gives the composition of the obtained product, in percent by weight.

TABLE I

| | CHARGE (% by weight) | PRODUCT (% by weight) |
|---|---|---|
| Methane | — | 0.03 |
| Ethane + ethylene | — | 0.07 |
| Propane | — | — |
| Propene | 0.12 | 1.10 |
| Normal butane | 16.24 | 17.10 |
| Isobutane | 4.73 | 4.78 |
| 1-Butene | 10.14 ⎫ 77.81 | 14.12 ⎫ 53.32 |
| 2-Butene | 67.67 ⎭ | 39.20 ⎭ |
| Isobutene | 1.10 | 23.60 |
| Polymers | — | — |

The results will be more clearly expressed by making use of the following definitions:

$$\text{Conversion rate \%} = \frac{\Delta[\text{n-butenes}]}{\Sigma[\text{n-butenes (at the input)}]}$$

$$\text{Selectivity to isobutene \%} = \frac{\Delta[\text{isobutene}]}{\Delta[\text{n-butenes}]}$$

$$\text{Polymerization selectivity \%} = \frac{\Sigma[C_5^+]}{\Delta[\text{n-butenes}]}$$

$$\text{Cracking selectivity \%} = \frac{\Sigma[C_1, C_2, C_3]}{\Delta[\text{n-butenes}]}$$

$$\text{Selectivity of hydrogen transfer \%} = \frac{\Delta[C_4(\text{paraf})]}{\Delta[\text{n-butenes}]}$$

The above symbols have the following definitions:

$\Delta[\text{n-butenes}] = \Sigma\text{n-butenes (at the input)} - \Sigma\text{n-butenes (at the output)}$ $\Delta[\text{isobutene}] = \text{isobutene (at the output)} - \text{isobutene (at the input)}$ $\Sigma(C_1, C_2, C_3) = \Sigma C_1, C_2, C_3$ saturated and unsaturated hydrocarbons $\Delta C_4(\text{paraf}) = \Sigma\text{butanes (output)} - \Sigma\text{butanes (input)}$ $C_5^+ = $ hydrocarbons having 5 carbon atoms and more.

The total conversion of 1- and 2-butenes is 31.5% (by weight).

The selectivities with respect to the converted butenes are as follows (expressed in percent by weight):

| | |
|---|---|
| Selectivity to isobutene | 91.9% |
| Polymerization selectivity | 0 |
| Cracking selectivity | 4.9% |
| Hydrogen transfer selectivity | 3.7% |

Ratio by weight between the total butenes at the output and at the input of the reactor (in %): 98.8%

Ratio by weight between the total C$_4$ cut a the output and at the input of the reactor (in %): 98.9%

Ratio by weight isobutene/C$_4$ cut (in %) (at the output of the reactor): 23.9%

Ratio by weight (in %) isobutene/ΣC$_4$ olefins (at the output of the reactor): 30.7%

Carbon content of the catalyst after 10 hours of run: 0.4%.

EXAMPLE 2

Example 1 is repeated while varying the space velocity and the molar ratio H$_2$O/HC.

Space velocity by volume of the liquid olefinic charge per volume of catalyst and per hour: 1
and
molar ratio H$_2$O/HC of the olefinic cut: 2.2

Table II below again reports the composition of the olefinic C$_4$ cut charge and also gives the composition of the product obtained after isomerization.

TABLE II

| | CHARGE (% by weight) | PRODUCT (% by weight) |
|---|---|---|
| Methane | — | 0.04 |
| Ethane + ethylene | — | 0.16 |
| Propane | — | 0.02 |
| Propene | 0.12 | 2.10 |
| Normal butane | 16.24 | 17.31 |
| Isobutane | 4.73 | 4.54 |
| 1-Butene | 10.14 ⎫ 77.81 | 11.80 ⎫ 46.00 |
| 2-Butene | 67.67 ⎭ | 34.20 ⎭ |
| Isobutene | 1.10 | 29.83 |
| Polymers | — | — |

The total conversion of 1- and 2-butenes, by weight is:

$$\frac{77.81 - 46}{77.81} \times 100 = 40.9\%$$

The selectivities with respect to the converted 1- and 2-butenes are as follows (expressed in % by weight):

| | |
|---|---|
| Selectivity to isobutene | 90.3% |
| Polymerization selectivity | 0 |
| Cracking selectivity | 7.3% |
| Hydrogen transfer selectivity | 2.8% |
| Ratio between the total butenes at the output and at the input of the reactor, in % by weight | 96.1% |
| Ratio between the total C$_4$ cut at the output and at the input of the reactor, in % by weight | 97.8% |
| Ratio isobutene/C$_4$ cut in % by weight (at the output of the reactor) | 30.5% |
| Ratio isobutene/ΣC$_4$ olefins, in % by weight (at the output of the reactor) | 39.3% |
| Carbon content of the catalyst after 10 hours of run | 0.3% |

EXAMPLE 3 (COMPARATIVE)

Example 1 is repeated except that the olefinic C$_4$ cut to isomerize is introduced in the reactor without addition of water.

In Table III, the composition of the charge and that of the isomerized product are reported.

TABLE III

| | CHARGE (% by weight) | PRODUCT (% by weight) |
|---|---|---|
| Methane | — | 0.39 |
| Ethane + ethylene | — | 1.2 |
| Propane | — | 0.35 |
| Propene | 0.12 | 8.2 |
| Normal butane | 16.24 | 17.9 |

TABLE III-continued

| | CHARGE (% by weight) | PRODUCT (% by weight) |
|---|---|---|
| Isobutane | 4.73 | 8.4 |
| 1-Butene | 10.14 ⎫ 77.81 | 11.83 ⎫ 37.54 |
| 2-Butene | 67.67 ⎭ | 25.71 ⎭ |
| Isobutene | 1.10 | 19.90 |
| Polymers | — | 6.12 |

The total conversion of 1- and 2-butenes is (by weight):

$$100 \times \frac{77.81 - 37.54}{77.81} = 51.7\%$$

The selectivities with respect to the converted 1- and 2-butenes are as follows (expressed in % by weight):

| | |
|---|---|
| Selectivity to isobutene | 46.7% |
| Polymerization selectivity | 15.2% |
| Cracking selectivity | 25.2% |
| Hydrogen transfer selectivity | 13.2% |
| Ratio between the total butenes at the output and at the input of the reactor, in % by weight | 72.8% |
| Ratio between the total C$_4$ cut at the output and at the input of the reactor in % by weight | 83.8% |
| Ratio isobutene/C$_4$ cut, in % by weight at the output of the reactor | 23.7% |
| Ratio isobutene/ΣC$_4$ olefins, in percent by weight at the output of the reactor | 34.6% |
| Carbon content of the catalyst after 10 hours of run | 25.5% |

This example shows that the absence of water results in a drop of the selectivity as well as in an excessive carbon deposit resulting in a quick deactivation of the catalyst.

The example is repeated with injection of a small amount of steam, the molar ratio $$\frac{H_2O}{HC \text{ of the olefinic charge}}$$

being equal to 0.05.

Substantially the same results as above are obtained.

EXAMPLE 4

1-pentene is treated under the operating conditions of example 1.

Among the products withdrawn from the reaction zone are found, in addition to linear pentenes, the desired isopentenes as well as cracking and polymerization products.

The obtained results are reported below:

| | |
|---|---|
| Conversion % by weight | 34.5% |

The selectivities of the converted pentene are:

| | |
|---|---|
| to isopentenes (% by weight) | 92.1% |
| Polymerization | 0 |
| Cracking (% by weight) | 5.1% |
| Hydrogen transfer (% by weight) | 3.4% |
| Carbon content of the catalyst after 10 hours of run | 0.5% |

EXAMPLE 5

Example 1 is repeated by making use of a catalyst containing 11% of silica instead of 3% in example 1. The palladium amount is 20 ppm and the balance to 100% is alumina. The results are reported in table IV.

TABLE IV

|  | CHARGE (% by weight) | PRODUCT (% by weight) |
|---|---|---|
| Methane | — | 0.06 |
| Ethane and ethylene | — | 0.03 |
| Propane | — | 0.06 |
| Propene | 0.12 | 2.40 |
| Normal butane | 16.24 | 17.50 |
| Isobutane | 4.73 | 4.80 |
| 1-Butene | 10.14 } 77.81 | 15.25 } 53.35 |
| 2-Butene | 67.67 | 38.10 |
| Isobutene | 1.10 | 21.60 |
| Polymers | — | 0.2 |

The total conversion of 1- and 2-butenes is (by weight):

$$\frac{77.81 - 53.35}{77.81} \times 100 = 31.44\%$$

The selectivities with respect to the converted butenes are as follows (expressed in % by weight):

| | |
|---|---|
| Selectivity to isobutene | 83.81% |
| Polymerization selectivity | 0.82 |
| Cracking selectivity | 9.93 |
| Hydrogen transfer selectivity | 5.44 |
| Ratio by weight between the total butenes at the output and at in the input of the reactor (in %) | 95 |
| Ratio by weight between the total $C_4$ cut and the output and the input of the reactor (in %) | 97.37 |
| Ratio by weight isobutene/$C_4$ cut (in %) (at the output of the reactor) | 22.21 |
| Ratio by weight (in %) isobutene/$\Sigma C_4$ olefins (at the output of the reactor) | 28.72 |
| Carbon content of the catalyst after 10 hours of run | 0.4% |

The comparison of examples 1 and 5 show that, with a too high proportion of silica (example 5):

the conversion is equivalent in both examples,
the selectivity to isobutene begins to decrease in example 5,
polymerization begins in example 5,
cracking increases in example 5.

It is further observed that, in example 5:
the hydrogen transfer also increases,
the butenes ratio output/input decreases,
the $\Sigma C_4$ ratio output/input decreases,
the ratio (reactor output) isobutene/$C_4$ cut decreases,
the ratio isobutene/$C_4$ olefins decreases,
and the carbon content increases.

What is claimed is:

1. A process for isomerizing a linear $C_{4-20}$ ethylenic hydrocarbon to a branched $C_{4-20}$ ethylenic hydrocarbon, comprising contacting an olefinic hydrocarbon charge containing said linear $C_{4-20}$ ethylenic hydrocarbon with steam and an isomerization catalyst; wherein said catalyst is an alumina catalyst which further comprises 0.5-10% by weight of silica, and 5 ppm-2% by weight of at least one metal or metal compound, said metal being palladium, chromium, nickel, copper, manganese or silver; and wherein the molar ratio $H_2O$/hydrocarbons is 0.1-10.

2. A process according to claim 1, wherein the molar ratio $H_2O$/hydrocarbons is 0.5-3.

3. A process according to claim 2, wherein the molar ratio $H_2O$/hydrocarbons is 0.8-2.7.

4. A process according to claim 1, wherein said metal is palladium, the palladium concentration being from 5 to 100 ppm, with respect to the catalyst.

5. A process according to claim 4, wherein said palladium concentration is from 10 to 30 ppm.

6. A process according to claim 1, effected at a temperature of 300°-500° C., a pressure of 0.05-1 MPa, and a space velocity, expressed in volume of liquid charge per volume of catalyst and per hour, of 0.1-10, said process being applied to the manufacture of isobutene, wherein said charge is a catalytic cracking effluent, a steam cracking effluent, a coking effluent, a thermal cracking effluent, a visbreaking effluent or a fraction from an effluent of a MTBE producing unit, said charge consisting at least in part of 1-butene and 2-butene.

7. A process according to claim 6, wherein said temperature is 400°-500° C., said pressure is 0.08-0.4 MPa, and said space velocity is 0.5-4.

8. A process according to claim 1, wherein said catalyst contains 2 to 4% by weight of silica.

9. A process according to claim 1, wherein said catalyst contains 1-6% by weight of silica.

10. A process according to claim 1, wherein said catalyst contains less than 0.1% by weight of alkali and alkaline earth metals.

11. A process according to claim 1, wherein said catalyst has a specific surface of 10-350 m²/g, and a pore volume of 0.4-0.8 cc/g.

12. A process according to claim 1, which is effected in the substantial absence of hydrogen gas.

* * * * *